US00PP37653P3

(12) United States Plant Patent
Bull

(10) Patent No.: US PP37,653 P3
(45) Date of Patent: Aug. 25, 2026

(54) ***ECHINACEA* PLANT NAMED 'BullEchipur 120'**

(50) Latin Name: *Echinacea purpurea*
Varietal Denomination: BullEchipur 120

(71) Applicant: Hartwig Bull, Gönnebek (DE)

(72) Inventor: Hartwig Bull, Gönnebek (DE)

( * ) Notice: Subject to any disclaimer, the term of this patent is extended or adjusted under 35 U.S.C. 154(b) by 0 days.

(21) Appl. No.: 19/235,179

(22) Filed: Jun. 11, 2025

(65) Prior Publication Data

US 2025/0386751 P1 Dec. 18, 2025

Related U.S. Application Data

(60) Provisional application No. 63/731,837, filed on Jun. 12, 2024.

(51) Int. Cl.
*A01H 5/02* (2018.01)
*A01H 5/12* (2018.01)
*A01H 6/14* (2018.01)

(52) U.S. Cl.
USPC ..... Plt./428
CPC ..... *A01H 6/1448* (2018.05); *A01H 5/02* (2013.01); *A01H 5/12* (2013.01)

(58) Field of Classification Search
USPC ..... Plt./428
CPC ..... A01H 5/02; A01H 5/00; A01H 6/1448; A01H 6/14
See application file for complete search history.

(56) References Cited

U.S. PATENT DOCUMENTS 7,982,110 B2 * 7/2011 Ren ..... A01H 5/12 800/300
PP31,064 P2 * 11/2019 Ren ..... A01H 5/02 Plt./428
PP35,164 P2 5/2023 Ren
PP35,286 P3 7/2023 Bull

OTHER PUBLICATIONS

ThinkPlants Catalog 2024-25 retrieved on Sep. 3, 2025 at https://online.flippingbook.com/view/530070179/34/, cover page, 2, 34-35, 88-89. (Year: 2025).*
Wist et al. Floral Structure and Dynamics of Nectar Production in *Echinacea pallida* var. *angustifolia* (*Asteraceae*), Int. J. Plant Sci. 169(6):708-722, 2008. (Year: 2008).*
Mills, 2024 New Perennial Varieties, Supplement to Greenhouse Management retrieved on Jan. 13, 2026 at https://www.gardencentermag.com/article/2024-new--perennial-varieties/ cover page, pp. 1-23 and back cover page (14 pp. total). (Year: 2024).*
Brookgreen Gardens *Echinacea purpurea* 'PAS702918', retrieved on Aug. 27, 2025 at https://www.brookgreen.ord/plantcollection/name/echinacea-purpurea-pas702918-powwow%25C2%25AE-white, 3 pages.

* cited by examiner

*Primary Examiner* — June Hwu
(74) *Attorney, Agent, or Firm* — The Webb Law Firm

(57) ABSTRACT

A new and distinct variety of *Echinacea* plant named 'BullEchipur 120' having a large flower, good growth habit, more uniformity, good branching plant, and good propagation rates.

1 Drawing Sheet

Botanical classification: *Echinacea purpurea.*
Varietal denomination: 'BULLECHIPUR 120'.

BACKGROUND OF THE INVENTION

The present invention relates to a new and distinct cultivar of *Echinacea*, botanically known as *Echinacea purpurea*, and hereinafter referred to by the name 'BullEchipur 120'.

The new *Echinacea* was discovered by the Inventor in August 2021, in a controlled environment in Gönnebek, Germany, as a part of a planned breeding program. The new *Echinacea* was selected on the basis of a new color, large flower, good growth habit, more uniformity, good branching plant, and good propagation rates.

Asexual propagation of the new cultivar by in vitro culture since September 2021, in Gönnebek, Germany, has shown that the unique features of this new *Echinacea* are stable and reproduced true to type in successive generations.

SUMMARY OF THE INVENTION

The following traits have been repeatedly observed and are determined to be unique characteristics of 'BullEchipur 120'. These characteristics in combination distinguish 'BullEchipur 120' as a new and distinct cultivar:

1. Compact growth
2. Watermelon flower color
3. Large flowers
4. More branching habit
5. Very uniform growth
6. Nice green leaves
7. Fast crop time
8. Early flowering In side-by-side comparisons conducted by the Inventor in Gönnebek, Germany, plants of the new *Echinacea* differed from plants of the female parent, 'Bul 2020-14' of *Echinacea purpurea*, in the following characteristics:

1. More compact
2. Watermelon flower color
3. Larger flowers
4. Medium branching
5. Green clean leaves
6. Earlier flowering In side-by-side comparisons conducted by the Inventor in Gönnebek, Germany, plants of the new *Echinacea* differed from plants of the male parent, 'Bul 2020-21' of *Echinacea purpurea*, in the following characteristics:

1. More compact
2. Watermelon flower color
3. More branches
4. Earlier flowering Plants of the new *Echinacea* can be compared to the plants of the *Echinacea* cultivar 'Cheyenne Spirit' (Patented, U.S. Pat. No. 7,982,110). In side-by-side comparisons conducted by the Inventor in Gönnebek, Germany, plants of the new *Echinacea* differed from plants of the cultivar 'Cheyenne Spirit' in the following characteristics:

1. More compact
2. More branching habit
3. Green clean leaves without necroses or brown spots
4. Even branching habit

DESCRIPTION OF THE DRAWINGS

The accompanying colored photographs illustrate the overall appearance of the new *Echinacea*, showing the colors as true as it is reasonably possible to obtain in colored reproductions of this type. Colors in the photographs may differ slightly from the color values cited in the detailed botanical description, which accurately describes the colors of the new *Echinacea*.

FIG. 1 comprises a top perspective view of a typical plant of 'BullEchipur 120' shown in natural lighting. The label '14-21' is an internal breeder designation.

DESCRIPTION OF THE PLANT

The cultivar *Echinacea* has not been observed under all possible environmental conditions. The phenotype may vary somewhat with variations in environment such as temperature and light intensity without, however, any variance in genotype.

The aforementioned photographs and following observations and measurements describe plants of the new *Echinacea* that were grown in an outdoor nursery in Gönnebek, Germany. During the production of the plants, temperatures averaged about 18-20° C. Plants used for the photographs and description were about 20 weeks from planting. Color references are made to The Royal Horticultural Society Colour Chart, 2015 version, except where general terms of ordinary dictionary significance are used.

PLANT

Botanical classification: *Echinacea purpurea.*
Parentage: 'Bul-2020-14' and 'Bul-2020-21'.
Propagation:

*Time to initiate roots.*—About 7 days.
*Time to develop roots.*—About 40-50 days.
*Time to produce a finished flowering plant.*—About 12 weeks.
*Root description.*—Lots of roots, free-branching, nice, healthy-looking root system.

Plant description:

*Growth rate/vigor.*—About 8 weeks to grow a young plant, and about 20 weeks to grow a finished plant, depending on whether conditions.
*Plant height.*—35-40 cm.
*Plant width.*—23-30 cm.
*Branching habit.*—Good branching, upright, shows a compact plant.
*Lateral branches.*—Number per plant: 12-20. Length: 2-25 cm. Diameter: 3-8 mm. Angle: Upright, outward. Strength: Strong. Texture: Pubescent. Color: 146C. Internode length: 1-5 cm.
*Foliage.*—Length: 3-20 cm. Width: 1-5.5 cm. Shape: Lanceolate. Shape of Apex: Acuminate. Shape of Base: Attenuate to Acute. Aspect: Straight to curved. Texture: Upper surface: Rough. Lower surface: Rough. Rugosity: Weak to medium. Young leaves: Upper surface color: 137A. Lower surface color: 137C. Fully expanded leaves: Upper surface color: 137A. Lower surface color: 137C. Venation: Type: Cross-venulate to longitudinal. Color: Upper surface: 145A. Lower surface: 145B. Margin: Entire.

Flowers:

*Bud.*—Stage of opening: Single type blossom. Shape: Elliptic shaped ray florets and tubular disk floret. Diameter: 1-3.5 cm. Length: 1.2-2.5 cm. Color: When closed: N137C. When open:
*Natural flowering season.*—10-12 weeks after planting.
*Inflorescence.*—Peduncle: single stem. Length: 7-10 cm. Color: 138C, up to a mix of a anthocyanin color 178A. Form: Single flower. Disc and ray floret arrangement: Single composite flower. Disc average height: 2.5-3.0 cm when mature. Average number per plant: 10-20. Average number per branch: 1-3. Fragrance: None. Diameter: 4-11 cm. Height: 2-4 cm. Diameter of disc: 1.5-4 cm. Receptacle height: 1 cm. Receptacle diameter: 1.5-4 cm. Ray florets: Number per inflorescence: 15-23. Arrangement: In two or three whorls. Attitude: When opening: Semi-erect. Mature: Horizontal to lightly semi-drooping. Cross-sectional profile: Immature: Moderate concave. Mature: Weakly concave, but mostly flat. Length: 1.5-5 cm. Width: 0.9-1.6 cm. Shape: Ellipse. Shape of Apex: Obtuse, notched as shallow (1.2 mm). Shape of Base: Acute. Margin: Entire. Texture: Upper surface: Smooth, glabrous. Lower surface: Rough. Color: When first opening: Upper surface: 39B. Lower surface: 159B. Immature: Upper surface 54B. Lower surface: 54C. At maturity: Upper surface: 54B. Lower surface: 54C. Ground color description: Watermelon. Disc florets: Number per inflorescence: Numerous, too many to count. Arrangement: In center of receptacle. Length: 8-15 mm. Width: 1-2 mm. Shape: Tubular. Shape of Apex: Sharp. Color: Immature receptacle spine with receptacle bracts: 185A. Mature receptacle spine with receptacle bracts: 45A. Phyllaries: Number per inflorescence: 35-50. Arrangement: In 3-4 whorls. Length: 0.5-1.5 cm. Width: 2-3 mm. Shape: Lanceolate. Shape of Apex: Elongate, oval. Shape of Base: Fused. Margin: Entire. Texture: Upper surface: Rough. Lower surface: Rough. Color: Immature: Upper surface: NN137C. Lower surface: NN137C. At maturity: Upper surface: NN137C. Lower surface: NN137C.

Reproductive organs:

*Androecium.*—Presence: On disk florets. Number: One. Filament: Length: 1-2 mm. Color: 45A. Anther: Shape: Oval. Length: 1 mm. Color: 45A. Pollen: Color: 15B. Amount: Too much to quantify.

*Gynoecium*.—Presence: In disk and ray florets. Pistil length: 1-2 mm. Stigma: Shape: Two parted. Color: 45A. Style: Length: 1-2 mm. Color: 45A.

*Seeds/fruit*.—Length: 1-2 mm. Color: Close to 164C.

Disease/pest resistance:

*Disease resistance*.—No additional disease resistance has been observed beyond the typical resistance in *Echinacea* plants.

*Pest resistance*.—No additional pest resistance has been observed beyond the typical resistance in *Echinacea* plants.

Weather tolerance:

*Temperature tolerance*.—No additional temperature resistance has been observed beyond the typical resistance in *Echinacea* plants.

*Drought tolerance*.—No additional drought resistance has been observed beyond the typical resistance in *Echinacea* plants.

I claim:

1. A new and distinct cultivar of *Echinacea* plant named 'BullEchipur 120', as herein illustrated and described.

* * * * *

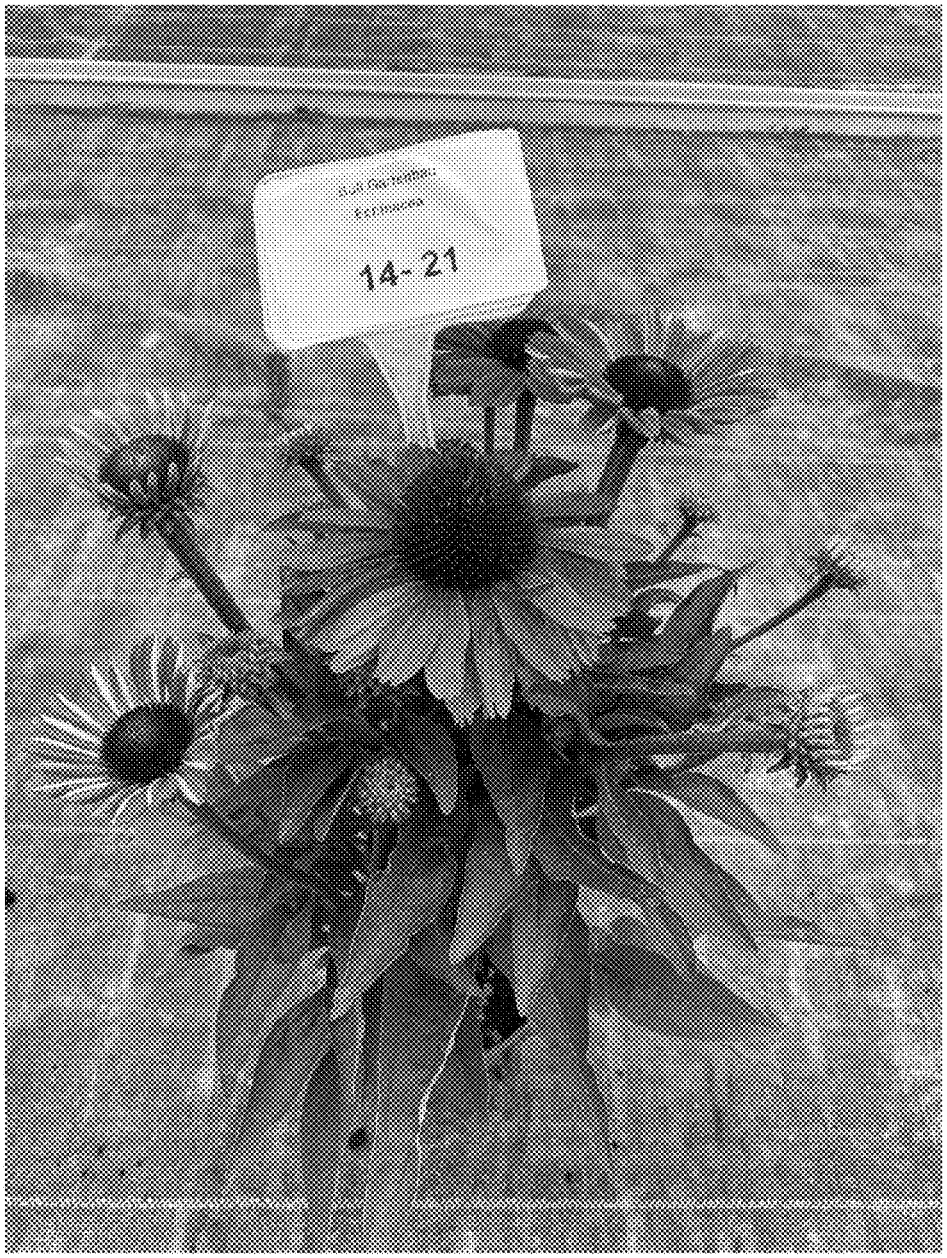
14-21